Figure 1:
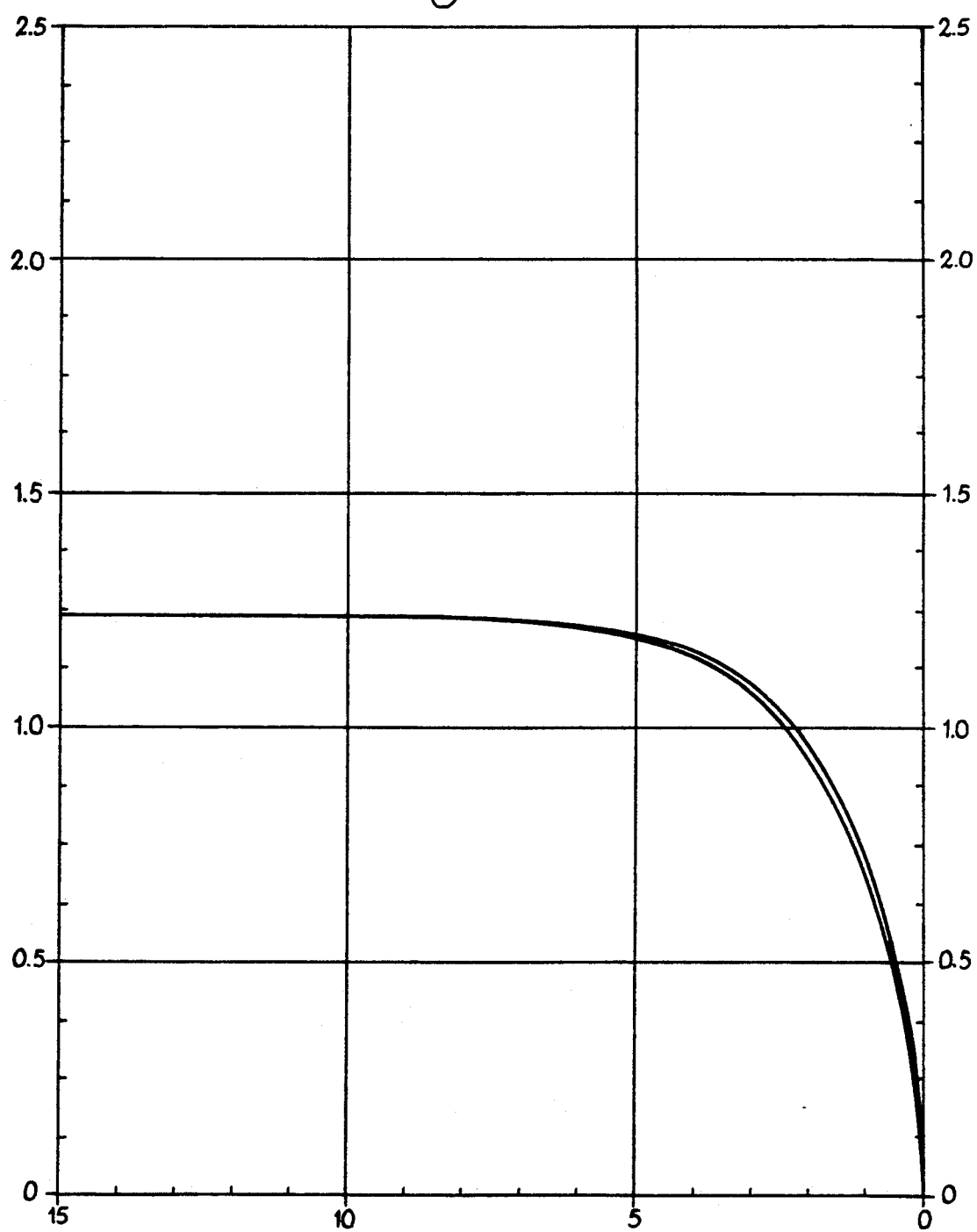

United States Patent [19]

Basagni et al.

[11] Patent Number: 5,077,199

[45] Date of Patent: Dec. 31, 1991

[54] READY TO USE LIQUID REAGENT FOR DETERMINING THE GLUCOSE CONTENT IN BLOOD

[75] Inventors: Umberto Basagni, Monte Savino-Arezzo; Francesco Bonicolini, Arezzo, both of Italy

[73] Assignee: A. Menarini S.a.S., Florence, Italy

[21] Appl. No.: 688,587

[22] Filed: Jan. 3, 1985

[30] Foreign Application Priority Data

Jan. 27, 1984 [IT] Italy .............................. 47603 A/84

[51] Int. Cl.$^5$ .................. C12Q 1/54; C12Q 1/26; C12Q 1/28; C12N 9/96
[52] U.S. Cl. ...................................... 435/14; 435/25; 435/188; 435/810; 435/28
[58] Field of Search .................... 435/14, 25, 28, 190, 435/810, 814, 188

[56] References Cited

U.S. PATENT DOCUMENTS

| | | | |
|---|---|---|---|
| 4,340,448 | 7/1982 | Schiller et al. | 435/14 |
| 4,473,638 | 9/1984 | Auditone-Hargreaves | 435/14 |
| 4,540,659 | 9/1985 | Litman et al. | 435/188 |

FOREIGN PATENT DOCUMENTS

| | | |
|---|---|---|
| 0024578 | 3/1981 | European Pat. Off. . |
| 0044432 | 1/1982 | European Pat. Off. . |
| 1592632 | 7/1981 | United Kingdom . |
| 8303254 | 9/1983 | World Int. Prop. O. . |

Primary Examiner—Esther M. Kepplinger
Attorney, Agent, or Firm—Brumbaugh, Graves, Donohue & Raymond

[57] ABSTRACT

Stable and ready to use liquid reagent for determining the glucose content in blood, comprising a glucose-oxidase free from catalase and a nonionic surface-active agent, such as, for example, the polyoxyethylene derivatives, hydroxypolyethylene ethoxydodecane, the lauryl ether of polyoxyethylene-glycol, as a stabilizer.

7 Claims, 3 Drawing Sheets

READY TO USE LIQUID REAGENT FOR DETERMINING THE GLUCOSE CONTENT IN BLOOD

The present invention relates to a ready to use liquid reagent for determining the glucose content in blood. More particularly, the invention relates to a stable liquid reagent, in a single kit ready to use, comprising a glucose-oxidase free from catalase and a nonionic surface-active agent.

It is known that the simplest and most used methods for determining the glucose content in blood (plasma or serum), are founded on the Trinder method or on variations of the same.

The glucose content in blood can be determined by means of the glucose-oxidase and the coloured Trinder reaction according to the following steps:

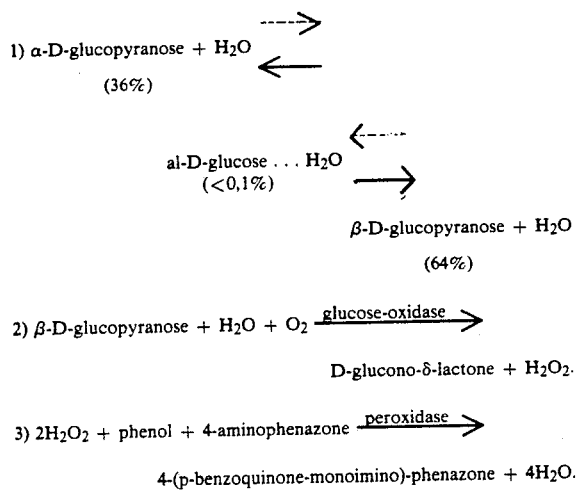

2) $\beta$-D-glucopyranose + $H_2O$ + $O_2$ $\xrightarrow{\text{glucose-oxidase}}$ D-glucono-$\delta$-lactone + $H_2O_2$.

3) $2H_2O_2$ + phenol + 4-aminophenazone $\xrightarrow{\text{peroxidase}}$ 4-(p-benzoquinone-monoimino)-phenazone + $4H_2O$.

The reagent consists of two components:
a) A suitably buffered enigmatic component (glucose-oxidase-peroxidase);
b) A chromogen, specifically 4-aminophenazone plus phenol (the latter can be replaced by its derivatives, hence the variations on the original method introduced by Trinder, who first used phenol).

All the reagents according to this method must be reconstituted at the moment of their use in a single operating reagent, having, when reconstituted, a limited stability.

It is to be noted that such a reagent, when reconstituted, presents the disadvantage of a guaranteed expiration date not longer than 60 days and of about 30 days average.

At present, two methods for reconstituting the operating reagent are known:
I) By adding water to a premixed enzymes-chromogen system;
II) By mixing the enzymatic component and the chromogen, which, in this case, have been kept apart.

However, in all cases, the user is required to manipulate the product. This operation, even if it is simple, frequently causes mistakes because in the reagent's preparation some technical problems affecting the system's validity can arise.

In the case I, when the operating reagent is reconstituted, high-purity distilled water is required, while only deionized water, not completely free from chlorine, is available in laboratories for clinical tests (common inconvenient, particularly in summer time).

In the case II, it may not be avoided, during the pouring off step, a loss of one of the two reagents due to the possible outflow of one of them, or, more frequently, to the incomplete dripping of one of the reagents from its bottle.

In such a case, the operating reagent often has a final concentration different from the desired one.

This disadvantage occurs also when the adopted procedure prevents from obtaining a complete mixture of the solute and the solvent, as it frequently occurs if the enzyme is provided as an anhydrous powder together with the buffer, which, being often a phosphate buffer, is slightly soluble.

When powdered reagents are used, as it frequently occurs, it must be taken into account that the powder ingredients proportion can be stated within a very broad range, and that an incomplete homogeneity can derive therefrom, even within the same preparation lot. This fact is even clearer when lyophilized enzymes are used, because, as it is known, the lyophllization process may often produce heterogeneously and causually reduce the enzymatic activity (the single bottle's position, with respect to its place on the plates during the freezing step, is surely influent), so that the final concentrations (as enzymatic activity) can be very different from each other. In addition to these technical inconvenients affecting the system's reliabillty, the reagents so far employed have a very high production costs.

The present production methods include two possibilities:
a) anhydrous powders
b) lyophiles.

In the case a) the production requires a special humidity-controlled room, and expensive plants, where the operators are exposed to serious risks due to the hard work conditions. This because the use of such enzymes as powders, and especially the presence of sodium azide and of the various buffers can cause damages, sometimes irreversible, to the respiratory organs of the operators, if they are exposed for a long time. Moreover, it has been noted that some people, after some years of this work, were sensitized to said enzymes, and subjected to the consequent injuries.

In the case b), the use of lyophilizers calls for large amounts of electrical energy and water, in addition to the plants extinction costs. It is therefore clear the importance of having available a reagent for determining the glucose content in blood which avoids the delicate reconstitution operations mentioned before, the expensive production techniques, which can be also dangerous for the staff, and the long lead-times (minimum time for reagent setup).

To solve this problem it is surprisingly proposed in this invention to use as a reagent a glucose oxidase (GOD), completely free from catalase, combined with stabilizers consisting of nonionic surface-active agents.

This combination provides a stable unitary liquid reagent ready to use. The homogeneous concentration of the single components' enzymatic activities appears to be particularly favourable, because the reaction rate, which can be expressed as $$\frac{\Delta A}{\Delta t}$$

of the coloured chromogen (A=absorbance or extinction), is particularly related to the ratio u.i/liter of glucose-oxidase, where u.i. is, as known, the amount of enzyme which oxidizes 1 μmole of glucose per min at 25° C. and pH=7.0 (sodium phosphate buffer).

About this subject it is to be observed that differences sometimes remarkable of the enzymatic activities can be found in reagents at present on the market, among bottles of the same lot too. Consequently there are some problems in the technique known as "Fixed Time", which can be properly carried out with a reagent like that according to this invention, whose invariability between the bottles is assured.

For a correct setting up of such a technique it is necessary that the glucose oxidation by "GOD" follows a pseudo-first-order kinetics with respect to β-glucose.

This causes a series of coupled reactions, to whom the kinetics principle of fixed time measurements can be applied.

The above-mentioned technique can be applied to the reagent according to this invention, making it particulary suitable to the fast analyzers, that allow to save much time.

It is therefore a specific object of this invention a ready to use liquid reagent for determining he glucose content in blood, characterized by comprising a glucose-oxidase free from catalase and a nonionic surface-active agent as a stabilizer. In a preferred embodiment according to the invention a glucose-oxidase amount of from 9,000 to 40,000 u.i/liter and a nonionic surface-active agent amount of from 5 mg/liter to 50 g/liter are employed. According to this invention, polyoxyethylene (POE) nonionic surface-active agents are preferably employed, such as POE-tridecyl alcohol, POE-nonylphenol, etc. (RENEX), POE-octylphenol (TRITON) and POE-lauryl-,cetyl-, stearyl-, oleyl-alcohol (BRIJ).

Similarly, very good results are obtained by employing, as a surface-active agent, hydroxypolyethyleneethoxydodecane ($C_{12}H_{25}$—(O—$C_2H_4$)$_n$—OH) or lauryl ether of polyoxyethylenglycol (THESIT).

It is to be pointed out that the absence of catalase was not taken into account either by Trinder nor by other authors.

For illustrative and not for limitative purposes the following compositions are now described:

| COMPOSITION A | Amounts referred to 1000 ml of reagent |
|---|---|
| GOD | 9,000–40,000 u.i |
| Peroxidase | 300–3,000 u.i. |
| 4-aminoantipyrine | 0.1–1.5 mmoles |
| Phenol | 1.5–15.5 mmoles |
| Phosphate buffer | pH 6.5–11.4 |

POE-lauryl alcohol (Brij 35 ), at a concentration of from 5 mg/liter to 50 g/liter has been employed in this composition as a surface-active agent.

| COMPOSITION B | Amounts referred to 1000 ml of reagent |
|---|---|
| GOD | 9,000–40,000 u.i. |
| Peroxydase | 300–3,000 u.i. |
| 4-aminoantipyrine | 0.1–1.5 mmoles |
| Phenol | 1.5–15.5 mmoles |
| Phosphate buffer | pH 6.5–11.4 |

POE-octylphenol (Triton-X100 ), at a concentration of from 5 mg/liter to 50 g/liter has been employed in this composition as a surface-active agent.

As it can be seen from the enclosed diagram (FIG. 1), wherein the absorbance values are plotted vs. the reaction times, the resulting reaction kinetics for the A and B compositions measured on Perkin-Elmer, is exactly alike when the employed surface-active agent is changed.

Figure 2:
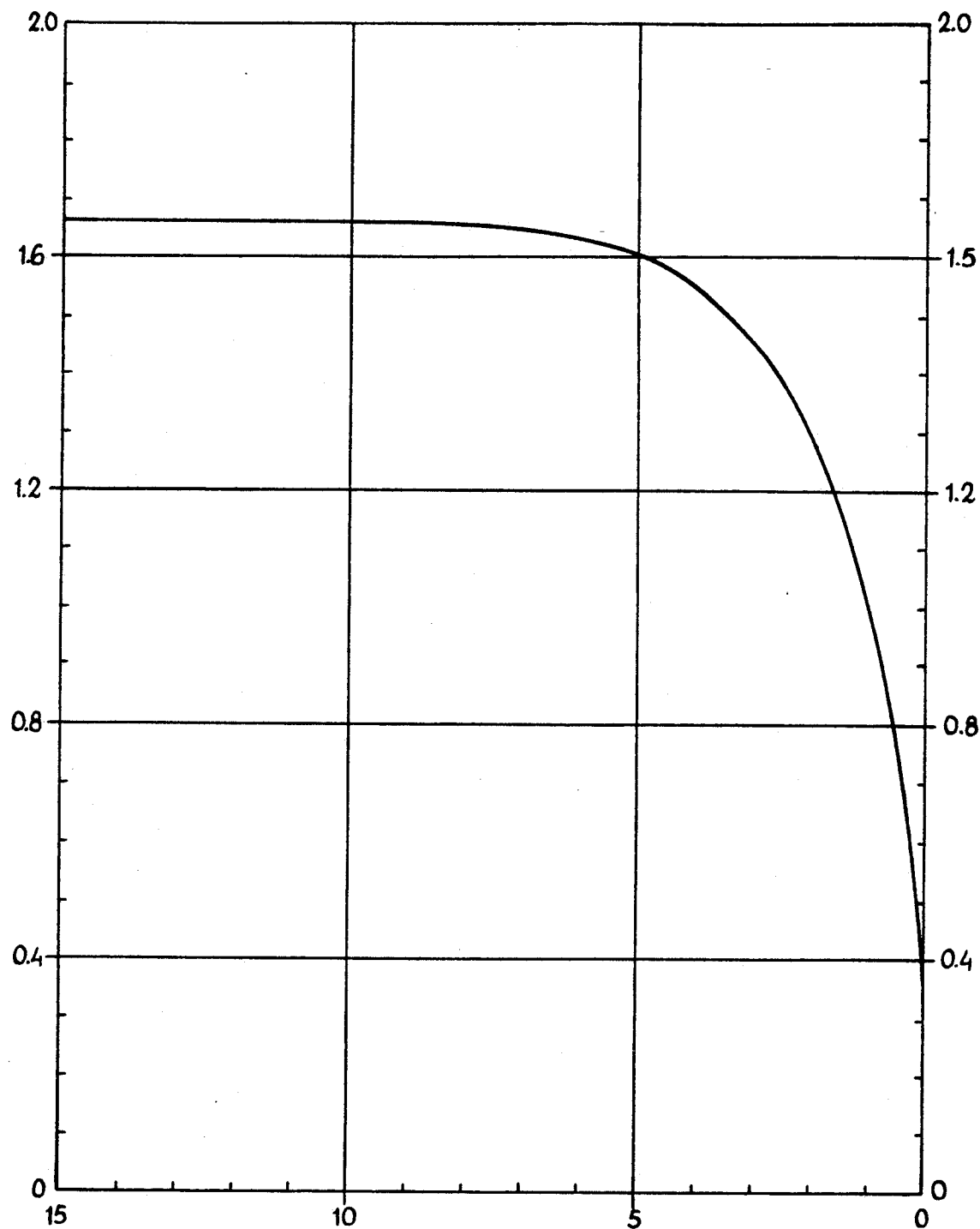

In order to show the unalterability of the product quality, the diagram of FIG. 2 depicts the absorbance of a reagent sample of the kind used in the A composition, prepared on February 1983 and tested on January 1984.

Besides noting how the curve is in accordance to the theory even at high concentration (500 mg/dl), it is to be considered that the reaction is completely accomplished within the estimated 10 minutes.

This result has been obtained by using a reagent lot as hereinbefore disclosed, stored, during said period, under stress test conditions (in fact a transparent vessel has been used instead of the opaque one usually requested, and the vessel has been often opened and closed again). It is further to be noted that the absorbance of white against $H_2O$ is only 0.128, that is quite an acceptable value from the moment that, moreover, such a reagent increases its absorbance under the direct action of the light.

TECHNICAL EXPERIMENT

Figure 3:
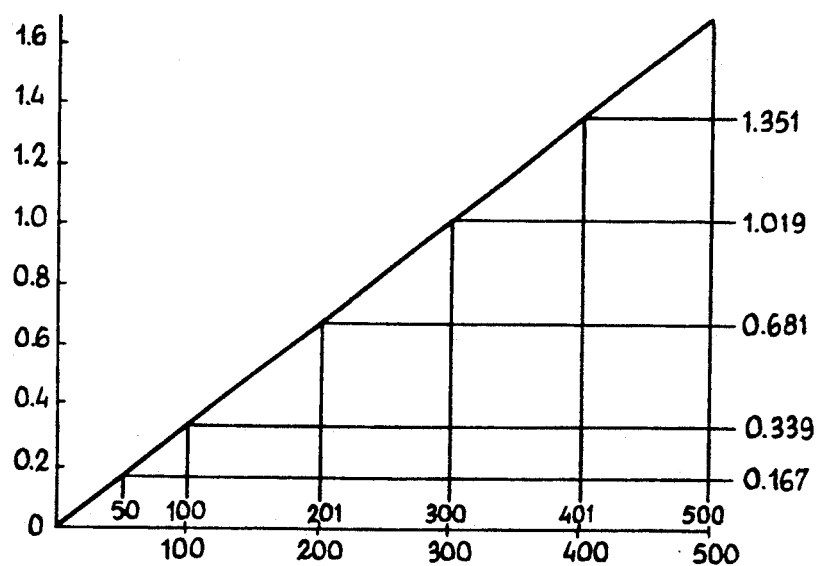

A graphic demonstration pertinent to the product cited for the diagram of FIG. 2 is given in FIG. 3, wherein the absorbance (A) is plotted as a function of the concentration (c.St.) of the standard employed (abscissa).

Said diagram clearly shows the perfect linearity of the reagent up to a maximum concentration of 500 mg/liter.

Said straight line has been plotted by the computer utilizing a series of standards of 25, 50, 100, 200, 400, 500 mg/liter.

The proportion of reagent to sample was 1,000 μliter/ 10 μliter; the reaction time was 10 minutes. The colour remains stable for about 1 hour.

The present invention has been disclosed with particular reference to some specific embodiments, but it is to be understood that modifications and changes can be introduced in the above disclosure by those skilled in the art without departing from its true spirit and scope.

We claim:

1. A ready-to-use aqueous liquid reagent for colorimetric determination of the glucose content in blood, comprising:
   (a) from 9,000 to 40,000 u.i/liter of enzymatically-active glucose oxidase free from catalase; and
   (b) from 5 mg/liter to 50 g/liter of a nonionic surface active agent effective to stabilize the liquid reagent.

2. A liquid reagent according to claim 1, wherein the surface active agent is a polyoxyethylene derivative.

3. A liquid reagent according to claim 2, wherein the surface active agent is polyoxyethylene-lauryl alcohol.

4. A liquid reagent according to claim 2, wherein the surface active agent is polyoxyethylene-octylphenol.

5. A liquid reagent according to claim 1, further comprising peroxidase and a chromogenic system such that upon combination of the reagent with a glucose-containing sample a colored product will be formed.

6. A liquid reagent according to claim 5, wherein the chromogenic system comprises phenol and 4-aminophenazone or a derivative thereof.

7. A liquid reagent according to claim 5, wherein the chromogenic system comprises phenol and 4-aminoantipyrine.

* * * * *